United States Patent
Penn et al.

(10) Patent No.: US 8,679,477 B2
(45) Date of Patent: *Mar. 25, 2014

(54) USE OF SDF-1 TO MITIGATE SCAR FORMATION

(71) Applicants: The Cleveland Clinic Foundation, Cleveland, OH (US); Juventas Therapeutics, Inc., Cleveland, OH (US)

(72) Inventors: Marc S. Penn, Beachwood, OH (US); Matthew Kiedrowski, Cleveland, OH (US); Rahul Aras, Broadview Heights, OH (US); Joseph Pastore, Mentor, OH (US)

(73) Assignees: The Cleveland Clinic Foundation, Cleveland, OH (US); Juventas Therapeutics, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/650,726

(22) Filed: Oct. 12, 2012

(65) Prior Publication Data

US 2013/0034523 A1    Feb. 7, 2013

Related U.S. Application Data

(62) Division of application No. 12/808,056, filed as application No. PCT/US2008/086820 on Dec. 15, 2008.

(60) Provisional application No. 61/013,878, filed on Dec. 14, 2007.

(51) Int. Cl.
*A61K 48/00* (2006.01)
*A61K 38/00* (2006.01)

(52) U.S. Cl.
USPC ............... 424/93.2; 514/44 R; 514/18.6

(58) Field of Classification Search
USPC .............. 424/93.2; 514/44 R, 18.6
See application file for complete search history.

(56) References Cited

U.S. PATENT DOCUMENTS

| | | | |
|---|---|---|---|
| 3,773,919 A | 11/1973 | Boswell et al. | |
| 5,197,985 A | 3/1993 | Caplan et al. | |
| 5,980,887 A | 11/1999 | Isner et al. | |
| 6,100,242 A | 8/2000 | Hammond et al. | |
| 6,121,246 A | 9/2000 | Isner | |
| 6,121,428 A | 9/2000 | Blank et al. | |
| 6,333,194 B1 * | 12/2001 | Levy et al. | 435/450 |
| 6,358,697 B2 | 3/2002 | Rothenberg et al. | |
| 6,387,369 B1 | 5/2002 | Pittenger et al. | |
| 6,479,654 B1 | 11/2002 | Baird et al. | |
| 6,676,937 B1 | 1/2004 | Isner et al. | |
| 6,818,210 B2 | 11/2004 | Field | |
| 7,101,708 B1 | 9/2006 | Lapidot et al. | |
| 7,125,856 B1 | 10/2006 | Isner | |
| 7,141,363 B2 | 11/2006 | Poznansky et al. | |
| 7,393,628 B2 | 7/2008 | Wagner et al. | |
| 7,393,830 B2 | 7/2008 | Shingo et al. | |
| 7,396,537 B1 | 7/2008 | Krupnick et al. | |
| 7,396,680 B2 | 7/2008 | Shmelkov et al. | |
| 7,399,740 B2 | 7/2008 | Eisenbach-Schwartz et al. | |
| 7,399,751 B2 | 7/2008 | Kirkpatrick et al. | |
| 7,402,567 B2 | 7/2008 | Chojkier et al. | |
| 7,402,724 B2 | 7/2008 | Conover | |
| 7,405,076 B2 | 7/2008 | Goldman et al. | |
| 7,405,195 B2 | 7/2008 | Chen et al. | |
| 7,662,392 B2 | 2/2010 | Itescu | |
| 2002/0039993 A1 | 4/2002 | Winchester et al. | |
| 2002/0061587 A1 | 5/2002 | Anversa | |
| 2002/0094327 A1 | 7/2002 | Petersen | |
| 2002/0107195 A1 | 8/2002 | Gupta | |
| 2002/0111290 A1 * | 8/2002 | Homey et al. | 514/1 |
| 2003/0017141 A1 | 1/2003 | Poznansky et al. | |
| 2003/0199464 A1 | 10/2003 | Itescu | |
| 2004/0037811 A1 | 2/2004 | Penn et al. | |
| 2004/0131585 A1 | 7/2004 | Itescu | |
| 2004/0235160 A1 | 11/2004 | Nishikawa et al. | |
| 2004/0258669 A1 | 12/2004 | Dzau et al. | |
| 2004/0258670 A1 | 12/2004 | Laughlin et al. | |
| 2005/0271639 A1 | 12/2005 | Penn et al. | |
| 2006/0105950 A1 | 5/2006 | Losordo | |
| 2006/0134070 A1 | 6/2006 | Mandrusov et al. | |
| 2006/0166361 A1 | 7/2006 | Seyda | |
| 2006/0182712 A1 | 8/2006 | Penn et al. | |
| 2007/0056595 A1 | 3/2007 | McLachlan | |

(Continued)

FOREIGN PATENT DOCUMENTS

| | | |
|---|---|---|
| EP | 1803464 A1 | 7/2007 |
| JP | 2004099471 | 2/2004 |

(Continued)

OTHER PUBLICATIONS

Badillo et al (J Surg Res. Nov. 2007; 143(1):35-42, online dated Oct. 16, 2007.*
Abbott et al (Circulation 2004, 110:3300-3305).*
Tang et al (Regulatory Peptides 125 (2005) 1-8.*
Zhang et al (J Mol Cell Cardiol Epub Dec. 7, 2007, 281-292).*
Zhang et al , FASEB J 2007; 21: 3197-207.*
Andreadis et al ( Trends in Biotechnology, 2006, 331-337.*
U.S. Appl. No. 13/556,595, filed Jul. 24, 2012, Penn.
U.S. Appl. No. 13/556,639, filed Jul. 24, 2012, Penn.
"Communication: Extended European Search Report", European Patent Office, Sep. 14, 2011, 6 pages.

(Continued)

*Primary Examiner* — Anoop Singh
(74) *Attorney, Agent, or Firm* — Baker & Hostetler LLP

(57) ABSTRACT

The subject matter provided herein relates to method for inhibiting or mitigating scar formation in a wound of the skin, by increasing the concentration of SDF-1 in, or proximate to, the wound. As described herein SDF-1 protein or an SDF-1 expression vector can be administered to a wound or the area proximate a wound by providing a therapeutically effective amount of SDF-1 protein or an SDF-1 expression vector.

12 Claims, 2 Drawing Sheets

(56) References Cited

U.S. PATENT DOCUMENTS

| | | | |
|---|---|---|---|
| 2007/0173471 A1 | 7/2007 | Losordo | |
| 2007/0224171 A1 | 9/2007 | Penn | |
| 2007/0258943 A1 | 11/2007 | Penn | |
| 2010/0166717 A1 | 7/2010 | Penn | |
| 2010/0272679 A1 | 10/2010 | Penn | |

FOREIGN PATENT DOCUMENTS

| | | | |
|---|---|---|---|
| WO | WO 92/08796 | | 5/1992 |
| WO | WO 94/28143 | | 12/1994 |
| WO | WO 99/20759 A | | 4/1999 |
| WO | WO 99/45775 A1 | | 9/1999 |
| WO | WO 99/50461 | | 10/1999 |
| WO | WO 00/15285 | | 3/2000 |
| WO | WO 00/19442 A1 | | 4/2000 |
| WO | WO 00/50048 A2 | | 8/2000 |
| WO | WO 00/60086 A2 | | 10/2000 |
| WO | WO 01/94420 | | 12/2001 |
| WO | WO 02/091995 | | 11/2002 |
| WO | WO 03/014336 | | 2/2003 |
| WO | WO 03/059375 | | 7/2003 |
| WO | WO 03/105908 | | 12/2003 |
| WO | WO 2004/017987 | | 3/2004 |
| WO | WO 2004/093688 | | 11/2004 |
| WO | WO 2005/047494 A | | 5/2005 |
| WO | WO 2005/116192 | | 12/2005 |
| WO | WO 2006/030887 | | 3/2006 |
| WO | WO/2006/030887 | * | 6/2006 |
| WO | WO 2008/121719 | | 10/2008 |
| WO | WO 2011/026041 A2 | | 3/2011 |
| WO | WO 2012/037083 A2 | | 3/2012 |

OTHER PUBLICATIONS

Abbott et al., "Stromel cell-derived factor-1alpha plays a critical role in stem cell recruitment to the heart after myocardial infarction but it is not sufficient to induce homing in the absence of injury", Circulation, Nov. 23, 2004, 110(21), 3300-3305.
Asahara et al., "VEGF Contributes to Postnatal Neovascularization by Mobilizing Bone Marrow-Derived Endothelial Progenitor Cells", EMBO J., 1999, vol. 18, 3964-3972.
Askari et al., "Effect of Stromal Cell-Derived Factor-1 on Stem-Cell Homing and Tissue Regeneration in Ischaemic Cardiomyopathy", The Lancet, Aug. 30, 2003, 362(9385), 697-703.
Badillo et al., "Lentiviral Gene Transfer of SDF-1a to Wounds Improves Diabetic Wound Healing", Journal of Surgical Research, Nov. 2007, 143(1), 35-42.
Bauman et al., "CXCR-4 Transduced Human Mesenchymal Stem Cells (MSCs) Migrate in Response to SDF-1alpha", Blood, 2001, 98(11-part 1), 87a.
Baumgartner et al., "Constitutive Expression of phVEGF165 After Intramuscular Gene Transfer Promotes Collateral Vessel Development in Patients With Critical Limb Ischemia", Circulation, 1998, 97, 1114-1123.
Cheng et al., "Targeted Migration of Mesenchymal Stem Cells Modified with CXCR4 Gene to Infarcted Myocardium Improves Cardiac Performance", Mol. Ther., 2008, 16, 571-579.
Cui et al., "Highly Efficient Gene Transfer into Murine Liver Achieved by Intravenous Administration of Naked Epstein-Barr Virus (EBV)-Based Plasmid Vectors", Gene Therapy, 2001, 8, 1508-1513.
Daley et al., Prospects for Stem Cell-Based Therapy, Cell, Feb. 22, 2008, 132(4), 544-548.
Deglurkar et al., Human Gene Therapy, Nov. 2006, 17, 1144-1151.
Deten et al., "Hematopoietic Stem Cells Do No Repair the Infarcted Mouse Heart", Cardiovascular Research, 2005, 65, 52-63.
Egawa et al., "The Earliest Stages of B Cell Development Require a Chemokine Stromal Cell-Derived Factor/Pre-B Cell Growth-Stimulating Factor", Immunity, Aug. 2001, 15, 323-334.
Elmadbouh et al., "Ex Vivo Delivered Stromal Cell-Derived Factor-1Alpha Promotes Stem Cell Homing and Induces Angiomyogenesis in the Infarcted Myocardium", Journal of Molecular and Cellular Cardiology, Apr. 2007, 42(4), 792-803.
Etzion et al., "Influence of Embryonic Cardiomyocyte Transplantation on the Progression of Heart Failure in a Rat Model of Extensive Myocardial Infarction", J. Mol. Cell Cardiol., 2001, 33, 1321-1330.
Freedman et al., "Therapeutic Angiogenesis for Coronary Artery Disease", Ann Intern. Med., 2002, 136(1), 54-71.
Gallagher et al., "Diabetic Impairments in NO-Mediated Endothelial Progenitor Cell Mobilization and Homing Are Reversed by Hyperoxia and SDF-1a", The Journal of Clinical Investigation, May 2007, 117(5), 1249-1259.
Ghadge et al., "SDF-1a as a Therapeutic Stem Cell Homing Factor in Myocardial Infarction", Pharmacology & Therapeutics, Jan. 2011, 129(1), 97-108.
Grines et al., "Angiogenic Gene Therapy (Agent) Trail in Patients with Stable Angina Pectoris", Circulation, 2002, 105(111), 1291-1297.
Haider et al., "IGF-1-Overexpressing Mesenchymal Stem Cells Accelerate Bone Marrow Stem Cell Mobilization via Paracrine Activation of SDF-1a/CXCR4 Signaling to Promote Myocardial Repair", Circulation Research, Nov. 21, 2008, 103(11), 1300-1398.
Hariawala et al., "VEGF Improves Myocardial Blood Flow But Produces EDRF-Mediated Hypotension in Porcine Hearts", J. Surg. Res., 1996, 63, 77-82.
Hattori et al., "Plasma Elevation of Stromal Cell-Derived Factor-1 Induces Mobilization of Mature and Immature Hematopoietic Progenitor and Stem Cells", Blood, 2001, 97, 3354-3360.
Hiasa et al., "Gene Transfer of Stromal Cell-Derived Factor-1a Enhances Ischemic Vasculogenesis and Angiogenesis via Vascular Endothelial Growth Factor/Endothelial Nitric Oxide Synthase-Related Pathway", Circulation, May 25, 2004, 1009, 2454-2461.
Holden et al., "Plasticity: Time for a Reappraisal?", Science, 2002, 296, 2126-2129.
Hu et al., "Design of Retroviral Vectors and Helper Cells for Gene Therapy", Pharmacological Reviews, Dec. 2000, 52(4), 493-511.
Hu et al., "Stomal Cell-Derived Factor-1α Confers Protection Against Myocardial Ischemia/Reperfusion Injury", Circulation 116:654-663, 2007.
Jackson et al., "Regeneration of Ischemic Cardiac Muscle and Vascular Endothelium by Adult Stem Cells", J. Clin. Invest., 2001, 107, 1395-1402.
Jain et al., "Cell Therapy Attenuates Deleterious Ventricular Remodeling and Improves Cardiac Performance After Myocardial Infarction", Circulation, 2001, 103, 1920-1927.
Jaleel et al., "Stromal Cell-Derived Factor-1 (SDF-1) Signaling Regulates Human Placental Trophoblast Cell Survival", Molecular Human Reproduction, Oct. 8, 2004, 10(12), 901-909.
Jo et al., Chemotaxis of Primitive hematopoietic Cells in Response to Stromal Cell-Derived Factor-1, J. Clin. Invest., Jan. 2000, 105(1), 101-111.
Kahn et al., "Overexpression of CXCR4 on Human CD34+ Progenitors Increases Their Proliferation, Migration and NOD/SCID Repopulation", Blood, Apr. 15, 2004, 103(8), 2942-2949.
Kanki et al., "Identification of Targeting Peptides for Ischemic Myocardium by in Vivo Phage Display", J. of Molecular and Cellular Cardiology, Feb. 24, 2011, 50, 841-848.
Kim et al., "In Vitro Behavior of Hematopoetic Progenitor Cells Under the Influence of Chemoattractants: Stromal Cell-Derived Factor-1, Steel Factor, and the Bone Marrow Environment", Blood, Jan. 1, 1998, 91(1), 100-110.
Kitaori et al., "Stromal Cell-Derived Factor 1/CXCR4 Signaling is Critical for the Recruitment of Mesenchymal Stem Cells to the Fracture Site During Skeletal Repair in a Mouse Model Arthritis & Rheumatism", Mar. 2009, 60(3), 813-823.
Koch et al., "Effect of Catheter-Based Transendocardial Delivery of Stromal Cell-Derived Factor 1a on Left Ventricular Function and Perfusion in a Porcine Model of Myocardial Infarction", Basic Research in Cardiology, Jan. 2006, 101(1), 69-77.
Kocher et al., "Neovascularization of Ischemic Myocardium by Human Bone-Marrow-Derived Angioblasts Prevents Cardiomyocyte Apoptosis, Reduces Remodeling and Improves Cardiac Function", Nat. Med., 2001, 7, 430-436.

(56) References Cited

OTHER PUBLICATIONS

Koh et al., "Differentiation and Long-Term Survival of C2C12 Myoblast Grafts in Heart", J. Clin. Invest., 1993, 92(3), 1548-1554.
Koh et al., "Targeted Expression of Transforming Growth Factor-Beta 1 in Intracardiac Grafts Promotes Vascular Endothelial Cell DNA Synthesis", J. Clin. Invest., 1995, 95, 114-121.
Konstan et al., "Compacted DNA Nanoparticles Administered to the Nasal Mucosa of Cystic Fibrosis Subjects are Safe and Demonstrate Partial to Complete Cystic Fibrosis Transmembrane Regulator Reconstitution", Human Gene Therapy, 2004, 15, 1-15.
Kusano et al., "Sonic Hedgehog Myocardial Gene Therapy: Tissue Repair Through Transient Reconstitution of Embryonic Signaling", Nature Medicine 11:1197-1204, 2005.
LaHam et al., "Local Perivascular Delivery of Basic Fibroblast Growth Factor in Patients Undergoing Coronary Bypass Surgery: Results of a Phase I Randomized, Double-Blind, Placebo-Controlled Trail", Circulation, 1999, 100, 1865-1871.
Lapidot et al., "Current Understanding of Stem Cell Mobilization: The Roles of Chemokines, Proteolytic Enzymes, Adhesion Molecules, Cytokines, and Stromal Cells", Experimental hematology, 2002, 30, 973-981.
Lataillade et al., "Stromal Cell-Derived Factor-1 Regulates Primitive Hematopoiesis by Suppressing Apoptosis and by Promoting G(0)/G(1) Transition in CD34(+) Cells: Evidence for an Autocrine/Paracrine Mechanism", Blood, Feb. 15, 2002, 99(4), 1117-1129.
Lee et al., "Functional Analysis of the Endothelin-1 Gene Promoter", The J. of Biological Chemistry, Jun. 1990, 265(18), 10446-10450.
Lee et al., "VEGF Gene Delivery to Myocardium: Deleterious Effects of Unregulated Expression", Circulation, 2000, 102(8), 898-901.
Li et al., "Cardiomyocyte Transplantation Improves Heart Function", Ann Thorac. Surg., 1996, 62, 654-660.
Li et al., "IL-8 Directly Enhanced Endothelial Cell Survival, Proliferation, and Matric Meallopproteinases Production and Regulated Angiogenesis", J. Immunol, 2003, 170:3369-3376.
Li et al., "Smooth Muscle Cell Transplantation into Myocardial Scar Tissue Improves Heart Function", J. Mol. Cell Cardiol., 1999, 31, 513, 522.
Lieber et al., "Integrating Adenovirus-Adeno-Associated Virus Hybrid Vectors Devoid of All Viral Genes", Journal of Virology, Nov. 1999, 73(11), 9314-9324.
Lopez et al., "Hemodynamic Effects of Intracoronary VEGF Delivery: Evidence of Tachyphylaxis and No Dependence of Response", Am. J. Physiol., 1997, 273, H1317-H1323.
Ma et al., "Impaired B-Lymphopoiesis, Myelopoiesis, and Derailed Cerebellar Neuron Migration in C", Proc. Natl. Acad. Sci, USA, 1998, 95, 9448-9453.
Matteucci et a., "Synthesis of Deoxyoligonucleotides on a Polymer Support", J. Am. Chem. Soc., 1981, 103, 3185-3191.
Menasche et al., "Myoblast Transplantation for Heart Failure", Lancet, 2001, 357, 279-280.
Miyoshi et al., "Development of a Self-Inactivating Lentivirus Vector", Journal of Virology, Oct. 1998, 72(10), 8150-8157.
Murry et al., "Haematopoietic Stem Cells Do Not Transdifferentiate Into Cardiac Myocytes in Myocardial Infarcts, Nature, Apr. 8, 204, 428(6983), 664-668, Epublication Mar. 21, 2004.
Nagasawa et al., "Defects of B-Cell Lymphopoiesis and Bone-Marrow Myelopoiesis in Mice Lacking the CXC Chemokine PBSF/SDF-1", Nature, 1996, 382, 635-638.
Nakayama et al., "Vascular Endothelial Growth Factor Synergistically Enhances Bone Morphogenetic Protein-4-Dependent Lymphohematopietic Cell Generation From Embryonic Stem Cells in Vitro", Blood, 2000, 95, 2275-2283.
Norol et al., "Influence of Mobilized Stem Cells on Myocardial Infarct Repair in a Nonhuman Primate Model", Blood, 2003, 102, 4361-4368.
Ohtsuka et al., Cytokine Therapy Prevents Left Ventricular Remodeling After Myocardial Infarction Through Neovascularization, FASEB, 2004, 18, 851-853.
Onai et al., "Impairment of Lymphopoiesis and Myelopoiesis in Mice Reconstituted with Bone Marrow-Hematopoietic Progenitor Cells Expressing SDF-1intrakine", Blood, 2000, 96, 2074-2080.
Orlic et al., "Bone Marrow Cells Regenerate Infarcted Myocardium", Nature, 2001, 410, 701-705.
Ortic et al., "Cytokine Mobilized CD34+ Cells Do Not Benefit Rhesus Monkeys Following Induced Myocardial Infarction", Blood, 2002, 100, 28a-29a, Abstract No. 94.
Ortic et al., "Mobilized Bone Marrow Cells Repair the Infarcted Heart, Improving Function and Survival", PNAS, 2001, 98, 10344-10349.
Peled et al., "The Chemokine SDF-1 Activates The Integrins LFA-1, VLA-4, and VLA-5 on Immature Human CD34(+) Cells: Role Transendothelial/Stromal Migration and Engraftment of NOD/SCID Mice", Blood, 2000, 95, 3289-3296.
Penn et al., "Autologous Cell Transplantation for the Treatment of Damaged Myocardium", Progress in Cardiovascular Diseases, Jul. 1, 2002, 45(1), 21-32.
Penn et al., Role of Stem Cell Homing in Myocardial Regeneration, International Journal of Cardiology, Jun. 2004, 95, S23-S25.
Perri et al., "Replicon Vectors Derived From Sindbus Virus and Semliki Forest Virus That Establish Persistant Replication in Host Cells", Oct. 2000, 74(20), 9802-9087.
Pfeffer et al., "Ventricular Remodeling After Myocardial Infarction. Experimental Observations and Clinical Implications", Circulation, 1990, 81, 1161-1172.
Quaini et al., "Chimerism of the Transplanted Heart", N. Engl. J. Med., 2002, 346(1), 5-15.
Rabbany et al., "Continuous Delivery of Stromal Cell-Derived Factor-1 From Alginate Scaffolds Accelerates Wound Healing", Cell Transplantation, 2010, 19(4), 399-408, Epublication Dec. 8, 2009.
Rosengart et al., "Angiogenesis Gene Therapy: Phase I Assessment of Direct Intramyocardial Administration of an Adenovirus Vector Expressing VEGF121 cDNA to Individuals with Clinically Significant Severe Coronary Artery Disease", Circulation, 1999, 100, 468-474.
Sakai et al., "Autologous Heart Cell Transplantation Improves Cardiac Function After Myocardial Injury", Ann Thorac. Surg., 1999, 68, 2074-2080.
Sakai et al., "Cardiothoracic Transplantation. Fetal Cell Transplantation: A Comparison of Three Cell Types", J. Thorac. Cardiovasc. Surg., 1999, 118(4), 715-725.
Sasaki et al., "Autologous Heart Cell Transplantation into Myocardial Scar Tissue Improves Heart Function", J. Mol. Cell Cardiol, Mar. 1999, 31(3), 513-522.
Sasaki et al., "Stromel Cell-Derived Factor-1 (SDF-1) Protects Deterioration of Cardiac Function Through Angiogenesis After Acute Myocardial Infarction (AMI) in Mice", Circulation, Oct. 26, 2004, 110(17), 111, $77^{th}$ Scientific Meeting of the American Heart Association, New Orleans, LA, Nov. 7-10, 2004, Abstract.
Schenk et al., "Monocyte Chemotactic Protein-3 is a Myocardial Mesenchymal Stem Cell Homing Factor", Stem Cells, Jan. 2007, 25(1), 245-251, EPublication Oct. 19, 2006.
Schuh et al., "Transplantation of Endothelial Progenitor Cells Improves Neovascularization and Left Ventricular Function After Myocardial Infarction in a Rat Model", Basic Res. Cardiol., Jan. 2008, 103(1), 69-77, EPublication Nov. 12, 2007.
Scorsin et al., "Comparison of the Effects of Fetal Cardiomyocyte and Skeletal Myoblast Transplantation on Postinfarction Left Ventricular Function", J. Thorac. Cardiovasc. Surg., 2002, 119, 1169-1175.
Shake et al., "Mesenchymal Stem Cell Implantation in a Swine Myocardial Infarct Model: Engraftment and Functional Effects", The Annals of Thoracic Surgical, Jun. 2002, 73(6), 1919-1925.
Simons et al., "Pharmacological Treatment of Coronary Artery Disease With Recombinant Fibroblast Growth Factor-2: Double-Blind, Randomized, Controlled Clinical Trail", Circulation, 2002, 105(7), 788-793.
Sundararaman, "Cell-Taught Gene Therapy for the Preservation and Regeneration of Cardiac Tissue Following Chronic Heart Failure", Thesis (Ph.D.), Cleveland State University, 2010, 1-209.

(56) References Cited

OTHER PUBLICATIONS

Suzuki et al., "Cell Transplantation for the Treatment of Acute Myocardial Infarction using Vascular Endothelial Growth Factor-Expressing Skeletal Myoblasts", Circulation, 2001, 104, I207-I212.

Tachibana et al., "The Chemokine Receptor CXCR4 is Essential for Vascularization of the Gastrointestinal Tract", Nature, 1998, 393, 591-594.

Tang et al., Mobilizing of Haematopoietic stem cells to ischemic myocardium by plasmid mediated stromal-cell-derived factor-1alpha (SDF-1alpha) treatment, Regulatory Peptides, 125(1-3):1-8, 2005.

Taylor et al., "Regenerating Functional Myocardium: Improved Performance After Skeletal Myoblast Transplantation", Nat. Med., Aug. 1998, 4, 929-933.

Tomita et al., "Improved Heart Function With Myogenesis and Angiogenesis After Autologous Porcine Bone Marrow Stromal Cell Transplantation", J. Thorac. Cadiovasc. Surg., 2002, 123, 1132-1140.

Topol, "Reperfusion Therapy for Acute Myocardial Infarction with Fibrinolytic Therapy or Combination Reduced Fibrinolytic Therapy and Platelet Glycoprotein IIB/IIIa Inhibition: The GUSTO V Randomised Trail", Lancet, 2001, 357, 1905-1914.

Udelson et al., "Therapeutic Angiogenesis With Recombinant Fibroblast Growth Factor-2 Improves Stress and Rest Myocardial Perfusion Abnormalities in Patients With Severe Symptomatic Chronic Coronary Artery Disease", Circulation, 2000, 102(14), 1605-1610.

Vale et al., "Randomized, Single-Blind, Placebo-Controlled Pilot Study of Catheter-Based Myocardial Gene Transfer for Therapeutic Angiogenesis Using Left Ventricular Electromechanical Mapping in Patients with Chronic Myocardial Ischemia", Circulation, 2001, 103, 2138-2143.

Van Royen et al., "Effects of local MCP-1 protein therapy on the development of the collateral circulation and atherosclerosis in Watanabe jyperlipidemic rabbits", Cardiovasc. Res. 57, 2003, 178-185.

Viswanathan, K et al., "Stress-induced enhancement of leukocyte trafficking into sites of surgery or immune activation", PNAS, Apr. 19, 2005, vol. 102, No. 16, 5805-5813.

Wagers et al., "Little Evidence for Developmental Plasticity of Adult Hematopoietic Stem Cells", Science, 2002, 297, 2256-2259.

Wright et al., "Hematopoietic Stem Cells are Uniquely Selective in Their Migratory Response to Chemokines", J. Exp. Med., 2002, 195(9), 1145-1154.

Yamaguchi et al., "Stomal Cell-Derived Factor-1 Effects on Ex Vivo Expanded Endothelial Progenitor Cell Recruitment for Ischemic Neovascularization", Circulation, Mar. 11, 2003, 107(9), 1322-1328.

Yano et al., "Stromal Cell-Derived Factor-1 (SDF-1)/CXCL12 Attenuates Diabetes in Mice and Promotes Pancreatic Beta-Cell Survival by Activation of the Prosurvival Kinase Akt", Diabetes, Dec. 2007, 56(12), 2946-2957.

Yau et al., "Enhanced Myocardial Angiogenesis by Gene Transfer With Transplanted Cells", Circulation, 2001, 104, I218-I222.

Yong et al., "Cord Blood Progenitor Cells Have Greater Transendothelial Migratory Activity and Increased Responses to SDF-1 and MIP-3beta Compared With Mobilized Adult Progenitor Cells", Br. J. Haematol., 1999, 107, 441-449.

Zhang et a., "Over-Expression of CXCR4 on Mesenchymal Stem Cells Augments Myoangiogenesis in the Infarcted Myocardium", J. Mol. Cell Cardiol., Feb. 2008, 44(2), 281-292, EPublication Dec. 7, 2007.

Zhang et al., "SDF-1 Expression by Mesenchymal Stem Cells Results in Trophic Support of Cardiac Myocytes After Myocardial Infarction", The FASEB Journal, Oct. 2007, 21(12), 3197-3207.

Zou et al., "Function of the Chemokine Receptor CXCR4 in Haematopoiesis and in Cerebellar Development", Nature, 1998, 393, 595-599.

Toksoy et al., "Biphasic expression of stromal cell-derived factor-1 during human wound healing", Journal of Dermatology, Jul. 2007, 1148-1154.

\* cited by examiner

US 8,679,477 B2

USE OF SDF-1 TO MITIGATE SCAR FORMATION

CROSS REFERENCE TO RELATED APPLICATIONS

This application is a division of U.S. application Ser. No. 12/808,056, filed Jun. 14, 2010, which is the U.S. national stage application of International Application No. PCT/US2008/086820, filed Dec. 15, 2008, which claims the benefit of U.S. Provisional Application No. 61/013,878, filed Dec. 14, 2007; the subject matter of each of these applications is incorporated by reference herein in its entirety.

TECHNICAL FIELD

The present invention relates to composition and methods of promoting wound healing in subject.

BACKGROUND

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified (Hunt, T. K., et al., "Coagulation and macrophage stimulation of angiogenesis and wound healing," in The Surgical Wound, pp. 1-18, ed. F. Dineen & G. Hildrick-Smith (Lea & Febiger, Philadelphia: 1981)].

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents generally are unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

SUMMARY

The present invention relates to methods and composition of treating and/or promoting wound healing in a subject. In the method, SDF-1 is administered directly to the wound or cells proximate the wound at an amount effective to promote wound healing. The wound can include any injury to any portion of the body of a subject. Examples of wounds that can be treated by the method include acute conditions or wounds; such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor associated wounds.

In an aspect of the invention, an amount of SDF-1 administered to the wound or cells proximate the wound can be an amount effective to promote or accelerate wound closure and wound healing, mitigate scar formation of and/or around the wound, inhibit apoptosis of cells surrounding or proximate the wound, and/or facilitate revascularization of the wounded tissue. The SDF-1 can be administered to cells proximate the wound that include SDF-1 receptors that are up-regulated as a result of tissue injury and/or trauma. In an aspect of the invention, the SDF-1 receptor can comprise CXCR4 and/or CXCR7, and the SDF-1 can be administered at an amount effect to increase Akt-phosphorylation of the cells.

In another aspect of the invention, the SDF-1 can be administered by expressing SDF-1 in cells proximate the wound and/or providing a pharmaceutical composition to the wound which includes SDF-1. The SDF-1 can be expressed from the cells proximate the wound by genetically modifying the cells by at least one of a vector, plasmid DNA, electroporation, and nanoparticles to express SDF-1.

The present invention also relates to methods and composition of inhibiting scar formation during wound healing in a subject. In the method, SDF-1 is administered directly to the wound or cells proximate the wound at an amount effective to mitigate scar formation in and/or around the wound. The wound can include any injury to any portion of the body of a subject. Examples of wound that can be treated by the method include acute conditions or wounds; such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, conditions related to diabetes and poor circulation, and all types of acne. In addition, the wound can include dermatitis such as impetigo, intertrigo, folliculitis and eczema, wounds following dental surgery; periodontal disease; wounds following trauma; and tumor associated wounds.

In an aspect of the invention, an amount of SDF-1 administered to the wound or cells proximate the wound can be an amount effective to promote or accelerate wound closure and wound healing, mitigate scar fibrosis of the tissue of and/or around the wound, inhibit apoptosis of cells surrounding or proximate the wound, and/or facilitate revascularization of the wounded tissue. The SDF-1 can be administered to cells proximate the wound that include SDF-1 receptors that are up-regulated as a result of tissue injury and/or trauma. In an aspect of the invention, the SDF-1 receptor can comprise CXCR4 and/or CXCR7, and the SDF-1 can be administered at an amount effect to increase Akt-phosphorylation of the cells.

In another aspect of the invention, the SDF-1 can be administered by expressing SDF-1 in cells proximate the wound and/or providing a pharmaceutical composition to the wound which includes SDF-1. The SDF-1 can be expressed from the cells proximate the wound by genetically modifying the cells by at least one of a vector, plasmid DNA, electroporation, and nanoparticles to express SDF-1.

The present invention further relates to methods and composition of promoting or accelerating wound closure in a subject. In the method, SDF-1 is administered directly to the wound or cells proximate the wound at an amount effective to promote wound closure. The wound can include any injury to any portion of the body of a subject. Examples of wound that can be treated by the method include acute conditions or wounds; such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, conditions related to diabetes and poor circulation, and all types of acne. In addition, the wound can include dermatitis such as impetigo, intertrigo, folliculitis and eczema, wounds following dental surgery; periodontal disease; wounds following trauma; and tumor associated wounds.

In an aspect of the invention, an amount of SDF-1 administered to the wound or cells proximate the wound can be an amount effective to promote or accelerate wound closure and wound healing, mitigate scar formation of and/or around the wound, inhibit apoptosis of cells surrounding or proximate the wound, and/or facilitate revascularization of the wounded tissue. The SDF-1 can be administered to cells proximate the wound that include SDF-1 receptors that are up-regulated as a result of tissue injury and/or trauma. In an aspect of the invention, the SDF-1 receptor can comprise CXCR4 and/or CXCR7, and the SDF-1 can be administered at an amount effect to increase Akt-phosphorylation of the cells.

In another aspect of the invention, the SDF-1 can be administered by expressing SDF-1 in cells proximate the wound and/or providing a pharmaceutical composition to the wound which includes SDF-1. The SDF-1 can be expressed from the cells proximate the wound by genetically modifying the cells by at least one of a vector, plasmid DNA, electroporation, and nanoparticles to express SDF-1.

The present invention still further relates to a topical and/or local formulation for promoting wound healing in subject. The formulation can include an amount of SDF-1 effective to promote wound closure and inhibit scarring of the wound when the formulation is administered to the wound.

The wound can include any injury to any portion of the body of a subject. Examples of wound that can be treated by the method include acute conditions or wounds; such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies, trauma-induced injuries including cuts, incisions, excoriations; injuries sustained from accidents; post-surgical injuries, as well as chronic conditions; such as pressure sores, bedsores, conditions related to diabetes and poor circulation, and all types of acne. In addition, the wound can include dermatitis such as impetigo, intertrigo, folliculitis and eczema, wounds following dental surgery; periodontal disease; wounds following trauma; and tumor associated wounds.

The amount of SDF-1 in the wound can also be an amount effective to promote or accelerate wound healing, mitigate scar formation of and/or around the wound, inhibit apoptosis of cells surrounding or proximate the wound, and/or facilitate revascularization of the wounded tissue. In an aspect of the invention, the SDF-1 can be in the form of protein or plasmid that when administered to a cell proximate the wound promotes expression of SDF-1 from the cells.

BRIEF DESCRIPTION OF THE DRAWINGS

The foregoing and other features of the present invention will become apparent to those skilled in the art to which the present invention relates upon reading the following description with reference to the accompanying drawings.

DETAILED DESCRIPTION OF ILLUSTRATIVE EMBODIMENTS

Figure 1:
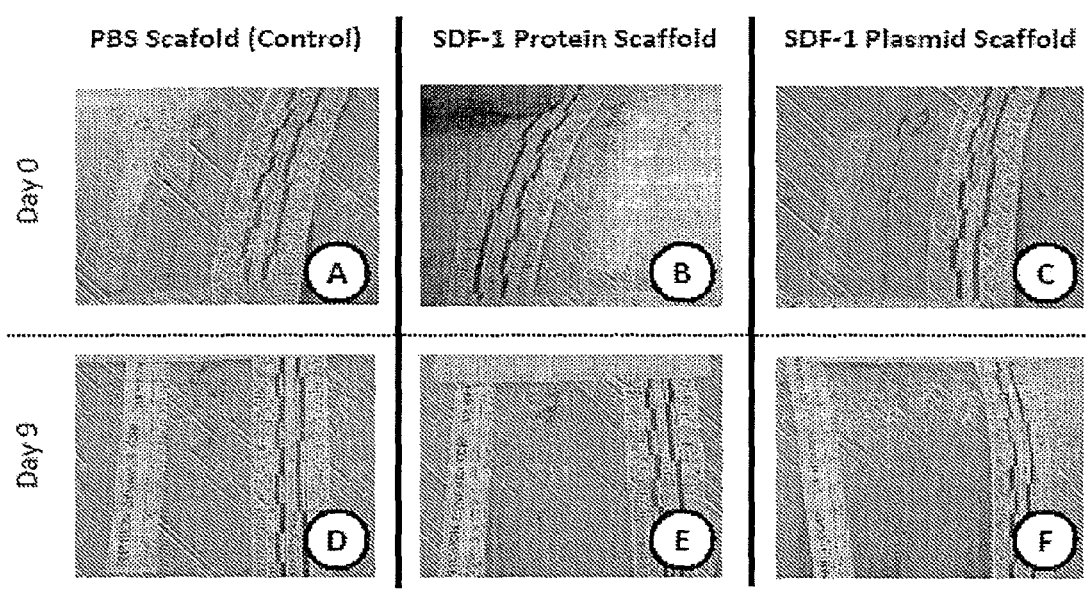
FIG. 1 illustrates photographs showing that SDF-1 releasing scaffolds accelerate wound healing.

Unless otherwise defined, all technical terms used herein have the same meaning as commonly understood by one of ordinary skill in the art to which this invention belongs. Commonly understood definitions of molecular biology terms can be found in, for example, Rieger et al., Glossary of Genetics: Classical and Molecular, 5th edition, Springer-Verlag: New York, 1991; and Lewin, Genes V, Oxford University Press: New York, 1994.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

The present invention relates to the treatment of a wound and/or the promotion of wound healing or wound closure in a mammalian subject by administering to the wound and/or cells proximate the wound an amount of SDF-1 effective to promote wound healing, mitigate cell apoptosis, and/or mitigate or inhibit scar formation in the wound. The present invention also relates to a method of inhibiting scar formation and/or fibrosis of a wound or tissue proximate a wound by administering to the wound and/or cells or tissue proximate the wound an amount of SDF-1 effective to promote wound healing, mitigate cell apoptosis, and/or mitigate or inhibit scar formation in the wound. The present invention further relates to a topical and/or local formulation for treating a wound comprising SDF-1 or an agent that upregulates expression of SDF-1 in cells of a wound.

The wound treated by the method and/or compositions of the present invention can include any injury to any portion of the body of a subject (e.g., internal wound or external wound) including: acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries, such as cuts, incisions, excoriations, injuries sustained as result of accidents, ulcers, such as pressure ulcers, diabetic ulcers, plaster ulcers, and decubitus ulcer, post-surgical injuries. The wound can also include chronic conditions or wounds, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; tumor associated wounds.

It will be appreciated that the present application is not limited to the preceding wounds or injuries and that other wounds or tissue injuries whether acute and/or chronic can be treated by the compositions and methods of the present invention.

As used herein, the term "promoting wound healing" or "promoting healing of a wound" mean augmenting, improving, increasing, or inducing closure, healing, or repair of a wound.

As used herein, the terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" of a wound includes increasing healing at a wound site, promoting wound closure, and decreasing scarring of the wound.

Mammalian subjects, which will be treated by methods and compositions of the present invention, can include any mammal, such as human beings, rats, mice, cats, dogs, goats, sheep, horses, monkeys, apes, rabbits, cattle, etc. The mammalian subject can be in any stage of development including adults, young animals, and neonates. Mammalian subjects can also include those in a fetal stage of development.

In accordance with an aspect of the invention, the SDF-1 can be administered to cells proximate the wound to mitigate apoptosis of the cells and promote wound healing, promote wound closure, and/or mitigate scar formation of and/or around the wound. The cells include cells that express SDF-1 receptors, which are upregulated as a result of trauma and/or tissue injury. The up-regulated SDF-1 receptors can include, for example, CXCR4 and/or CXCR7. It was found that sustained localized administration of SDF-1 to cells with up-regulated SDF-1 receptors as a result of tissue injury increases Akt phosphorylation in the cells which in turn can mitigate apoptosis of the cells. Additionally, long-term localized administration of SDF-1 to tissue facilitates recruitment of stem cells and/or progenitor cells, such as endothelial progenitor cells, expressing CXCR4 and/or CXCR7 to the site of the wound being treated, which can facilitate revascularization of the tissue surrounding and/or proximate the wound.

In one example, the period of time that the SDF-1 is administered to the cells of the wound and/or proximate the wound can comprise from about onset of the wound and/or tissue injury to about days, weeks, or months after tissue injury. It was found that topical and/or local SDF-1 delivery by protein or plasmid to wounds was sufficient to increase the rate of healing and wound closure. Moreover, the SDF-1 treated wounds tended to have less fibrosis than non-SDF-1 treated wounds, which suggests SDF-1 can mitigate scarring in treated wounds. It was also found that immediately after onset of tissue injury, cells in the wound tissue or about the periphery or the border of the wound up regulate expression of SDF-1. After about 24 hours, SDF-1 expression by the cells is reduced. The SDF-1 can be administered after the SDF-1 is reduced to mitigate apoptosis of the cells.

SDF-1 in accordance with the present invention can have an amino acid sequence that is substantially similar to a native mammalian SDF-1 amino acid sequence. The amino acid sequence of a number of different mammalian SDF-1 protein are known including human, mouse, and rat. The human and rat SDF-1 amino acid sequences are about 92% identical. SDF-1 can comprise two isoforms, SDF-1 alpha and SDF-1 beta, both of which are referred to herein as SDF-1 unless identified otherwise.

The SDF-1 can have an amino acid sequence substantially identical to SEQ ID NO: 1. The SDF-1 that is over-expressed can also have an amino acid sequence substantially similar to one of the foregoing mammalian SDF-1 proteins. For example, the SDF-1 that is over-expressed can have an amino acid sequence substantially similar to SEQ ID NO: 2. SEQ ID NO: 2, which substantially comprises SEQ ID NO: 1, is the amino acid sequence for human SDF-1 and is identified by GenBank Accession No. NP954637. The SDF-1 that is over-expressed can also have an amino acid sequence that is substantially identical to SEQ ID NO: 3. SEQ ID NO: 3 includes the amino acid sequences for rat SDF and is identified by GenBank Accession No. AAF01066.

The SDF-1 in accordance with the present invention can also be a variant of mammalian SDF-1, such as a fragment, analog and derivative of mammalian SDF-1. Such variants include, for example, a polypeptide encoded by a naturally occurring allelic variant of native SDF-1 gene (i.e., a naturally occurring nucleic acid that encodes a naturally occurring mammalian SDF-1 polypeptide), a polypeptide encoded by an alternative splice form of a native SDF-1 gene, a polypeptide encoded by a homolog or ortholog of a native SDF-1 gene, and a polypeptide encoded by a non-naturally occurring variant of a native SDF-1 gene.

SDF-1 variants have a peptide sequence that differs from a native SDF-1 polypeptide in one or more amino acids. The peptide sequence of such variants can feature a deletion, addition, or substitution of one or more amino acids of a SDF-1 variant. Amino acid insertions are preferably of about 1 to 4 contiguous amino acids, and deletions are preferably of about 1 to 10 contiguous amino acids. Variant SDF-1 polypeptides substantially maintain a native SDF-1 functional activity. Examples of SDF-1 polypeptide variants can be made by expressing nucleic acid molecules within the invention that feature silent or conservative changes. One example of an SDF-1 variant is listed in U.S. Pat. No. 7,405,195, which is herein incorporated by reference in its entirety.

SDF-1 polypeptide fragments corresponding to one or more particular motifs and/or domains or to arbitrary sizes, are within the scope of the present invention. Isolated peptidyl portions of SDF-1 can be obtained by screening peptides recombinantly produced from the corresponding fragment of the nucleic acid encoding such peptides. For example, an SDF-1 polypeptides of the present invention may be arbitrarily divided into fragments of desired length with no overlap of the fragments, or preferably divided into overlapping fragments of a desired length. The fragments can be produced recombinantly and tested to identify those peptidyl fragments, which can function as agonists of native CXCR-4 polypeptides.

Variants of SDF-1 polypeptides can also include recombinant forms of the SDF-1 polypeptides. Recombinant polypeptides preferred by the present invention, in addition to SDF-1 polypeptides, are encoded by a nucleic acid that can have at least 70% sequence identity with the nucleic acid sequence of a gene encoding a mammalian SDF-1.

SDF-1 variants can include agonistic forms of the protein that constitutively express the functional activities of native SDF-1. Other SDF-1 variants can include those that are resistant to proteolytic cleavage, as for example, due to mutations, which alter protease target sequences. Whether a change in the amino acid sequence of a peptide results in a variant having one or more functional activities of a native SDF-1 can be readily determined by testing the variant for a native SDF-1 functional activity.

The SDF-1 nucleic acid that encodes the SDF-1 protein can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand. The nucleic acid coding sequence that encodes SDF-1 may be substantially similar to a nucleotide sequence of the SDF-1 gene, such as nucleotide sequence shown in SEQ ID NO: 4 and SEQ ID NO: 5. SEQ ID NO: 4 and SEQ ID NO: 5 comprise, respectively, the nucleic acid sequences for human SDF-1 and rat SDF-1 and are substantially similar to the nucleic sequences of GenBank Accession No. NM199168 and GenBank Accession No. AF189724. The nucleic acid coding sequence for SDF-1 can also be a different coding sequence which, as a result of the redundancy or degeneracy of the genetic code, encodes the same polypeptide as SEQ ID NO: 1, SEQ ID NO: 2, and SEQ ID NO: 3.

Other nucleic acid molecules that encode SDF-1 within the invention are variants of a native SDF-1, such as those that encode fragments, analogs and derivatives of native SDF-1. Such variants may be, for example, a naturally occurring allelic variant of a native SDF-1 gene, a homolog or ortholog of a native SDF-1 gene, or a non-naturally occurring variant of a native SDF-1 gene. These variants have a nucleotide sequence that differs from a native SDF-1 gene in one or more bases. For example, the nucleotide sequence of such variants can feature a deletion, addition, or substitution of one or more nucleotides of a native SDF-1 gene. Nucleic acid insertions are preferably of about 1 to 10 contiguous nucleotides, and deletions are preferably of about 1 to 10 contiguous nucleotides.

In other applications, variant SDF-1 displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue (e.g., serine or threonine), for (or by) a hydrophobic residue (e.g., leucine, isoleucine, phenylalanine, valine or alanine); (b) a cysteine or proline for (or by) any other residue; (c) a residue having an electropositive side chain (e.g., lysine, arginine, or histidine), for (or by) an electronegative residue (e.g., glutamine or aspartine); or (d) a residue having a bulky side chain (e.g., phenylalanine), for (or by) one not having a side chain, (e.g., glycine).

Naturally occurring allelic variants of a native SDF-1 gene within the invention are nucleic acids isolated from mammalian tissue that have at least 70% sequence identity with a native SDF-1 gene, and encode polypeptides having structural similarity to a native SDF-1 polypeptide. Homologs of a native SDF-1 gene within the invention are nucleic acids isolated from other species that have at least 70% sequence identity with the native gene, and encode polypeptides having structural similarity to a native SDF-1 polypeptide. Public and/or proprietary nucleic acid databases can be searched to identify other nucleic acid molecules having a high percent (e.g., 70% or more) sequence identity to a native SDF-1 gene.

Non-naturally occurring SDF-1 gene variants are nucleic acids that do not occur in nature (e.g., are made by the hand of man), have at least 70% sequence identity with a native SDF-1 gene, and encode polypeptides having structural similarity to a native SDF-1 polypeptide. Examples of non-naturally occurring SDF-1 gene variants are those that encode a fragment of a native SDF-1 protein, those that hybridize to a native SDF-1 gene or a complement of to a native SDF-1 gene under stringent conditions, and those that share at least 65% sequence identity with a native SDF-1 gene or a complement of a native SDF-1 gene.

Nucleic acids encoding fragments of a native SDF-1 gene within the invention are those that encode, amino acid residues of native SDF-1. Shorter oligonucleotides that encode or hybridize with nucleic acids that encode fragments of native SDF-1 can be used as probes, primers, or antisense molecules. Longer polynucleotides that encode or hybridize with nucleic acids that encode fragments of a native SDF-1 can also be used in various aspects of the invention. Nucleic acids encoding fragments of a native SDF-1 can be made by enzymatic digestion (e.g., using a restriction enzyme) or chemical degradation of the full-length native SDF-1 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding a SDF-1 fusion protein may also be used in the invention. Such nucleic acids can be made by preparing a construct (e.g., an expression vector) that expresses a SDF-1 fusion protein when introduced into a suitable target cell. For example, such a construct can be made by ligating a first polynucleotide encoding a SDF-1 protein fused in frame with a second polynucleotide encoding another protein such that expression of the construct in a suitable expression system yields a fusion protein.

The nucleic acids encoding SDF-1 can be modified at the base moiety, sugar moiety, or phosphate backbone, for example, to improve stability of the molecule, hybridization, etc. The nucleic acids within the invention may additionally include other appended groups such as peptides (e.g., for targeting target cell receptors in vivo), or agents facilitating transport across the cell membrane, hybridization-triggered cleavage. To this end, the nucleic acids may be conjugated to another molecule, (e.g., a peptide), hybridization triggered cross-linking agent, transport agent, hybridization-triggered cleavage agent, etc.

The SDF-1 can be administered directly to the wound, about the periphery of the wound or to cells proximate, the wound in order to mitigate apoptosis of cells proximate the wound and facilitate angiogenesis to the wounded area as well as accelerate wound closure and inhibit scarring of the wound. The SDF-1 can be delivered to the wound or cells proximate the wound by administering an SDF-1 protein to the wound or cells, or by introducing an agent into target cells that causes, increases, and/or upregulates expression of SDF-1 (i.e., SDF-1 agent). The SDF-1 protein expressed in the target cells can be an expression product of a genetically modified cell. The target cells can include cells within or about the periphery of the wound or ex vivo cells that are biocompatible with tissue being treated. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the tissue being treated. The cells can include cells that are provided in skin grafts, bone grafts, engineered tissue, and other tissue replacement therapies that are used to treat wounds.

The agent can comprise natural or synthetic nucleic acids, according to present invention and described above, that are incorporated into recombinant nucleic acid constructs, typically DNA constructs, capable of introduction into and replication in the cell. Such a construct can include a replication system and sequences that are capable of transcription and translation of a polypeptide-encoding sequence in a given target cell.

Other agents can also be introduced into the cells to promote expression of SDF-1 from the cells. For example, agents that increase the transcription of a gene encoding SDF-1, increase the translation of an mRNA encoding SDF-1, and/or those that decrease the degradation of an mRNA encoding SDF-1 could be used to increase SDF-1 protein levels. Increasing the rate of transcription from a gene within a cell can be accomplished by introducing an exogenous promoter upstream of the gene encoding SDF-1. Enhancer elements, which facilitate expression of a heterologous gene, may also be employed.

Other agents can further include other proteins, chemokines, and cytokines, that when administered to the target cells can upregulate expression SDF-1 form the target cells. Such agents can include, for example: insulin-like growth factor (IGF)-1, which was shown to upregulate expression of SDF-1 when administered to mesenchymal stem cells (MSCs) (Circ. Res. Nov. 21, 2008; 103(11):1300-98); sonic hedgehog (Shh), which was shown to upregulate expression of SDF-1 when administered to adult fibroblasts (Nature Medicine, Volume 11, Number 11, November 23); transforming growth factor .beta. (TGF-.beta.); which was shown to upregulate expression of SDF-1 when administered to human peritoneal mesothelial cells (HPMCs); IL-1.beta., PDG-BF, VEGF, TNF-.alpha., and PTH, which are shown to upregulate expression of SDF-1, when administered to primary human osteoblasts (HOBS) mixed marrow stromal cells (BMSCs), and human osteoblast-like cell lines (Bone, 2006, April; 38(4): 497-508); thymosin .beta.4, which was shown to upregulate expression when administered to bone marrow cells (BMCs) (Curr. Pharm. Des. 2007; 13(31):3245-51; and hypoxia inducible factor 1.alpha. (HIF-1), which was shown to upregulate expression of SDF-1 when administered to bone marrow derived progenitor cells (Cardiovasc. Res. 2008, E. Pub.). These agents can be used to treat specific wounds or injuries where such cells capable of upregulating expression of SDF-1 with respect to the specific cytokine are present or administered.

One method of introducing the agent into a target cell involves using gene therapy. Gene therapy in accordance with the present invention can be used to express SDF-1 protein from a target cell in vivo or in vitro.

In an aspect of the invention, the gene therapy can use a vector including a nucleotide encoding an SDF-1 protein. A "vector" (sometimes referred to as gene delivery or gene transfer "vehicle") refers to a macromolecule or complex of molecules comprising a polynucleotide to be delivered to a target cell, either in vitro or in vivo. The polynucleotide to be delivered may comprise a coding sequence of interest in gene therapy. Vectors include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use in the present invention include viral vectors, lipid based vectors and other non-viral vectors that are capable of delivering a nucleotide according to the present invention to the target cells. The vector can be a targeted vector, especially a targeted vector that preferentially binds to cells of proximate the wound. Viral vectors for use in the invention can include those that exhibit low toxicity to a target cell and induce production of therapeutically useful quantities of SDF-1 protein in a tissue-specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the SDF-1 protein and is replication-defective in humans.

Other viral vectors that can be use in accordance with the present invention include herpes simplex virus (HSV)-based vectors. HSV vectors deleted of one or more immediate early genes (IE) are advantageous because they are generally noncytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the invention. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and an SDF-1 nucleic acid. In methods of delivery to cells proximate the wound, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Examples of lentiviral vectors include nucleic acid sequences required for vector propagation as well as a tissue-specific promoter operably linked to a SDF-1 gene. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates the secretion of a SDF-1 gene product from the target cell.

To combine advantageous properties of two viral vector systems, hybrid viral vectors may be used to deliver a SDF-1 nucleic acid to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable SDF-1 gene expression.

Other nucleotide sequence elements which facilitate expression of the SDF-1 gene and cloning of the vector are further contemplated. For example, the presence of enhancers upstream of the promoter or terminators downstream of the coding region, for example, can facilitate expression.

In accordance with another aspect of the present invention, a tissue-specific promoter, can be fused to a SDF-1 gene. By fusing such tissue specific promoter within the adenoviral construct, transgene expression is limited to a particular tissue. The efficacy of gene expression and degree of specificity provided by tissue specific promoters can be determined, using the recombinant adenoviral system of the present invention.

In addition to viral vector-based methods, non-viral methods may also be used to introduce a SDF-1 nucleic acid into a target cell. A review of non-viral methods of gene delivery is provided in Nishikawa and Huang, Human Gene Ther. 12:861-870, 2001. An example of a non-viral gene delivery method according to the invention employs plasmid DNA to introduce a SDF-1 nucleic acid into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent SDF-1 nucleic acid transfer into target cells (e.g., cardiomyocytes). In addition, preformed cationic liposomes or cationic lipids may be mixed with plasmid DNA to generate cell-transfecting complexes. Methods involving cationic lipid formulations are reviewed in Feigner et al., Ann N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the invention. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Additionally, the SDF-1 nucleic acid can be introduced into the target cell by transfecting the target cells using electroporation techniques. Electroporation techniques are well known and can be used to facilitate transfection of cells using plasmid DNA.

Vectors that encode the expression of SDF-1 can be delivered to the target cell in the form of an injectable preparation containing pharmaceutically acceptable carrier, such as saline, as necessary. Other pharmaceutical carriers, formulations and dosages can also be used in accordance with the present invention.

Where the target cell comprises a cell proximate the wound being treated, the vector can be delivered by direct injection at an amount sufficient for the SDF-1 protein to be expressed to a degree which allows for highly effective therapy. By injecting the vector directly into or about the periphery of the wound, it is possible to target the vector transfection rather effectively, and to minimize loss of the recombinant vectors. This type of injection enables local transfection of a desired number of cells, especially about the wound, thereby maximizing therapeutic efficacy of gene transfer, and minimizing the possibility of an inflammatory response to viral proteins.

Where the target cell is a cultured cell that is later transplanted into wound (e.g., tissue graft), the vectors can be delivered by direct injection into the culture medium. A SDF-1 nucleic acid transfected into cells may be operably linked to a regulatory sequence.

The transfected target cells can then be transplanted to the wound by well known transplantation techniques, such as graft transplantation. By first transfecting the target cells in vitro and then transplanting the transfected target cells to the wound, the possibility of inflammatory response in the tissue proximate the wound is minimized compared to direct injection of the vector into cells proximate the wound.

SDF-1 can be expressed for any suitable length of time within the target cell, including transient expression and stable, long-term expression. In one aspect of the invention, the SDF-1 nucleic acid will be expressed in therapeutic amounts for a defined length of time effective to mitigate apoptosis in the cells proximate the wound and/or to promote stem cell or progenitor cell homing to the wound. This amount of time can be that amount effect to promote healing of the wound, accelerate closure of the wound, and/or inhibit scar formation.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins and nucleic acids can be determined readily determined by one skilled in the art using the experimental methods described below.

The SDF-1 protein or agent, which causes, increases, and/or upregulates expression of SDF-1 from target cells, can be administered to the cells of the wound, cells proximate wound, or cells administered to the wound (e.g., MSCs transfected to express SDF-1) neat or in a pharmaceutical composition. The pharmaceutical composition can provide localized release of the SDF-1 or agent to the cells proximate the wound, cells being treated, or cells administered to the wound. Pharmaceutical compositions in accordance with the invention will generally include an amount of SDF-1 or agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations that can be used for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the SDF-1 or agent. The slow release formulations are typically implanted in the vicinity of the wound site, for example, at the site of cell expressing CXCR4 and/or CXCR7 in or about the wound.

Examples of sustained-release preparations include semipermeable matrices of solid hydrophobic polymers containing the SDF-1 or agent, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers, such as ethylene-vinyl acetate and lactic acid-glycolic acid enable release of molecules for over 100 days, certain hydrogels release proteins for shorter time periods. When encapsulated, SDF-1 or the agent can remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the SDF-1 or agent. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 p.m. Sonication of MLVs results in the formation of small unilamellar vesicles (SUVs) with diameters in the range of 200 to 500 .ANG., containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

For preparing pharmaceutical compositions from the compounds of the present invention, pharmaceutically acceptable carriers can be in any suitable form (e.g., solids, liquids, gels, etc.). A solid carrier can be one or more substances which may also act as diluents, flavoring agents, binders, preservatives, and/or an encapsulating material.

In another aspect of the present invention, the SDF-1 or SDF-1 agent can be formulated for topical administration to treat surface wounds. Topical formulations include those for delivery via the mouth (buccal) and to the skin such that at least one layer of skin (i.e., the epidermis, dermis, and/or subcutaneous layer) is contacted with SDF-1 or agent. Topical delivery systems may be used to administer topical formulations of the present invention.

Formulations for topical administration to the skin can include ointments, creams, gels, and pastes comprising SDF-1 or SDF-1 agent to be administered in a pharmaceutically acceptable carrier. Topical formulations can be prepared using oleaginous or water-soluble ointment bases, as is well known to those in the art. For example, these formulations may include vegetable oils, animal fats, and more preferably semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases may also be used including, for example, glycol ethers and derivatives, polyethylene glycols, polyoxyl 40 stearate, and polysorbates.

In another aspect of the invention, SDF-1 or agent can be provided in and/or on a substrate, solid support, and/or wound dressing for delivery of the SDF-1 or agent to the wound. As used herein, the term "substrate," or "solid support" and "wound dressing" refer broadly to any substrate when prepared for, and applied to, a wound for protection, absorbance, drainage, etc. The present invention may include any one of the numerous types of substrates and/or backings that are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer). The shape and size of a wound may be determined and the wound dressing customized for the exact site based on the measurements provided for the wound. As wound sites can vary in terms of mechanical strength, thickness, sensitivity, etc., the substrate can be molded to specifically address the mechanical and/or other needs of the site. For example, the thickness of the substrate may be minimized for locations that are highly innervated, e.g., the fingertips. Other wound sites, e.g., fingers, ankles, knees, elbows and the like, may be exposed to higher mechanical stress and require multiple layers of the substrate.

In one example, the substrate can be a bioresorbable implant that includes a polymeric matrix and the SDF-1 or agent dispersed in the matrix. The polymeric matrix may be in the form of a membrane, sponge, gel, or any other desirable configuration. The polymeric matrix can be formed from biodegradable polymer. It will be appreciated, however, that the polymeric matrix may additionally comprise an inorganic or organic composite. The polymeric matrix can comprise any one or combination of known materials including, for example, chitosan, poly(ethylene oxide), poly(lactic acid), poly(acrylic acid), poly(vinyl alcohol), poly(urethane), poly (N-isopropyl acrylamide), poly(vinyl pyrrolidone) (PVP), poly(methacrylic acid), poly(p-styrene carboxylic acid), poly (p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(caprolactone), polylactide, poly(ethylene), poly(propylene), poly(glycolide), poly(lactide-co-glycolide), poly (amide), poly(hydroxylacid), poly(sulfone), poly(amine), poly(saccharide), poly(HEMA), poly(anhydride), collagen, gelatin, glycosaminoglycans (GAG), poly(hyaluronic acid), poly(sodium alginate), alginate, hyaluronan, agarose, polyhydroxybutyrate (PHB), and the like.

It will be appreciated that one having ordinary skill in the art may create a polymeric matrix of any desirable configuration, structure, or density. By varying polymer concentration, solvent concentration, heating temperature, reaction time, and other parameters, for example, one having ordinary skill in the art can create a polymeric matrix with any desired physical characteristic(s). For example, the polymeric matrix may be formed into a sponge-like structure of various densities. The polymeric matrix may also be formed into a membrane or sheet which could then be wrapped around or otherwise shaped to a wound. The polymeric matrix may also be configured as a gel, mesh, plate, screw, plug, or rod. Any conceivable shape or form of the polymeric matrix is within the scope of the present invention. In an example of the present invention, the polymeric matrix can comprise a alginate matrix.

In another aspect of the present invention, at least one progenitor cell can be provided in the polymeric matrix. Examples progenitor cells can be selected from, but not restricted to, totipotent stem cell, pluripotent stem cell, multipotent stem cell, mesenchymal stem cell, neuronal stem cell, hematopoietic stem cell, pancreatic stem cell, cardiac stem cell, embryonic stem cell, embryonic germ cell, neural crest stem cell, kidney stem cell, hepatic stem cell, lung stem cell, hemangioblast cell, and endothelial progenitor cell. Additional examples of progenitor cells can be selected from, but not restricted to, de-differentiated chondrogenic cells, myogenic cells, osteogenic cells, tendogenic cells, ligamentogenic cells, adipogenic cells, and dermatogenic cells.

The polymeric matrix of the present invention may be seeded with at least one progenitor cell and the SDF-1 or agent. The SDF-1 or agent can be dispersed in matrix and/or expressed from the seeded progenitor cell. Progenitor cells can include autologous cells; however, it will be appreciated that xenogeneic, allogeneic, or syngeneic cells may also be used. Where the cells are not autologous, it may be desirable to administer immunosuppressive agents in order to minimize immunorejection. The progenitor cells employed may be primary cells, explants, or cell lines, and may be dividing or non-dividing cells. Progenitor cells may be expanded ex vivo prior to introduction into the polymeric matrix. Autologous cells are preferably expanded in this way if a sufficient number of viable cells cannot be harvested from the host.

The SDF-1 or SDF-1 agent can also be provided in or on a surface of a medical device used to treat an internal and/or external wound. The medical device can comprise any instrument, implement, machine, contrivance, implant, or other similar or related article, including a component or part, or accessory, which is, for example, recognized in the official U.S. National Formulary, the U.S. Pharmacopoeia, or any supplement thereof; is intended for use in the diagnosis of disease or other conditions, or in the cure, mitigation, treatment, or prevention of disease, in humans or in other animals; or, is intended to affect the structure or any function of the body of humans or other animals, and which does not achieve any of its primary intended purposes through chemical action within or on the body of man or other animals, and which is not dependent upon being metabolized for the achievement of any of its primary intended purposes.

The medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either implantable pacemakers or defibrillators, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, surgical tissue extractors, transition sheaths and dilators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, cardiac valves, and tissue engineered constructs, such as bone grafts and skin grafts.

The following examples are for the purpose of illustration only and are not intended to limit the scope of the claims, which are appended hereto.

Example 1

Stromal Cell-Derived Factor-1 Release in Alginate Scaffolds: Characterization and Ability to Accelerate Wound Healing We hypothesized that a slow-release delivery of either SDF-1 protein or plasmid would increase its effectiveness on wound healing. Therefore, we employed a clinically-relevant delivery system, an alginate scaffold, to deliver SDF-1 over time to a porcine acute surgical wound model. We characterize SDF-1 delivery using alginate scaffolds in vitro, and demonstrated the potential for therapeutic benefit in vivo by using the scaffolds to deliver SDF-1 protein and plasmid to acute surgical wounds.

Preparation of Scaffolds for In Vivo Application

For the in vivo application, custom 1 cm×6 cm alginate scaffolds were produced by the same process described above. Scaffolds were then loaded with SDF-1 plasmid (n=6), SDF-1 protein (n=10), or phosphate buffered saline (PBS) (n=4) by the process described below.

For the SDF-1 plasmid scaffolds, a plasmid was created by inserting the gene encoding human SDF-1 in a pcDNA3.1 backbone (Invitrogen Corporation, Carlsbad, Calif.). A loading solution was prepared by mixing 3.5 mg of the SDF-1 plasmid in 2.33 ml PBS to create a 1.5 mg/ml solution. On each scaffold, the loading solution was pipetted under sterile conditions onto the scaffold in six 60 µl drops (360 µl total) equally spaced so that each drop covered a 1 cm×1 cm area of the scaffold.

For the SDF-1 protein scaffolds, a loading solution was prepared by mixing 10 µg of carrier-free SDF-1 protein (R&D systems, Minneapolis, Minn.) with 5 mL PBS and 3 ml of 1000 IU/ml injection heparin (Baxter Healthcare Corporation, Deerfield, Ill.) to create a 1.5 µg/ml solution. On each scaffold, the loading solution was pipetted under sterile conditions onto the scaffold in six equally spaced 60 µl drops.

The PBS scaffolds served as a negative control. The loading solution was prepared by mixing 1.35 mL PBS and 0.45 ml of 1000 IU/ml injection heparin. The loading solution was pipetted under sterile conditions onto the scaffold in six equally spaced 60 µl drops.

All loaded scaffolds were stored at 4° C. for 12 hours prior to applying them to the wounds.

Porcine Surgical Wound Healing Model and Ante-Mortem Follow-Up

In 2 Domestic Yorkshire pigs, general anesthesia was induced. A cuffed endotracheal tube was placed and general anesthesia was maintained with isoflurane delivered in oxygen through a rebreathing system with ventilator assist. A standard model of acute surgical wounds was used. Each animal received twelve (12) 5 cm full thickness incisions (six on each side of the spine) spaced approximately 7.5 cm apart. Each incision was made perpendicular to the spine, starting 7.5 cm from the spine and cutting toward the abdomen. Gauze was placed in the incision until the bleeding stopped. The gauze was removed, and the incision was sutured closed.

Following wound closure, the scaffold was placed next to the wound and photographed (FIG. 1). On each pig, the scaffold placement order was randomized with the following distribution:

SDF-1 protein scaffold (n=5)
SDF-1 plasmid scaffold (n=3)
PBS scaffold (control, n=2)
No scaffold (sham, n=2)

The scaffold was placed over the wound (except in the sham group), and each wound was dressed with a Tegaderm™ patch.

To determine the effect of SDF-1 on the rate of wound healing, wound length was measured by the same veterinarian at day 0 (prior to scaffold placement) and prior to sacrifice. Wound length was converted to Percent Healing by the following relationship:

(Initial wound length-final wound length)/initial wound length*100%

To monitor both the acute and chronic effects of SDF-1 on wound healing, the acute effects were evaluated in the first pig, which was sacrificed at 4 days, and the chronic effects in the second which was sacrificed at 9 days.

Post-Mortem Follow-Up

Following sacrifice, one section from the middle of each wound site was excised for histopathological and immunohistochemical analysis. Standard hematoxylin and eosin (H&E) stain was used to assess extent of fibroplasia, inflammation, and necrosis at day 4 and necrosis, fibrosis, and granulomatous inflammation at day 9. Each parameter was graded on a qualitative scale by a histopathologist blinded to randomization as either: none (not present), minimal, mild, moderate, or severe. Immunohistochemical staining was performed on the same tissue section. The effect of SDF-1 on fibroblast infiltration into the wound was detected by vimentin staining. The effect on blood vessel formation was determined by CD31 and the presence of smooth muscle was detected by smooth muscle actin staining. The amount of each stain per sample was graded by the same pathologist using the same qualitative scale as above (minimal severe).

Figure 2:
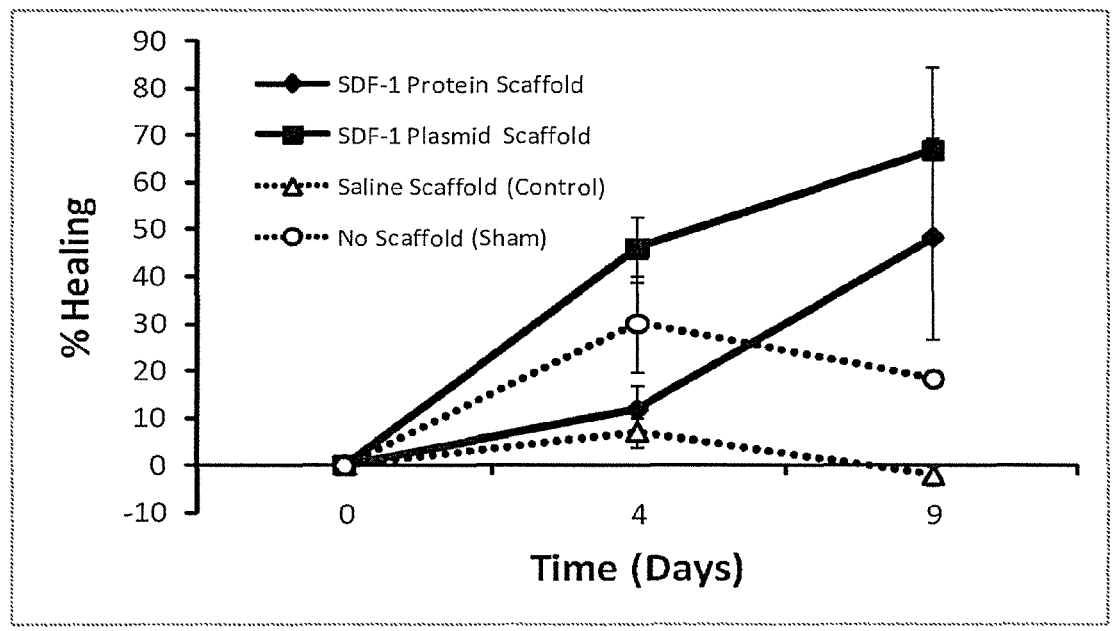
FIG. 2 illustrates plots showing the % Healing over a period days for porcine wounds treated with SDF-1 protein scaffold, SDF-1 plasma scaffold, Saline scaffold, and no scaffold.

The impact of an SDF-1-releasing scaffold on wound healing is also shown in FIGS. 1 and 2. FIG. 1 shows representative examples of wounds treated with control (PBS) scaffold, SDF-1 protein scaffold, and SDF-1 plasmid scaffold at day 0 (top panel) and day 9 (bottom panel). All full-incision wounds (middle) have a length 5.0±0.1 cm.

At day 9, the wound treated with the control scaffold is still apparent, and has a Percent Healed of 0%. In contrast, both the SDF-1 protein and SDF-1 plasmid treated wounds are no longer visible at day 9, and both have a Percent Healed of 100%.

FIG. 2 summarizes the percent healing data for all treated wounds. Day 4 data is from the first pig, and Day 9 data is from the second pig. At Day 9, the wounds treated with either the SDF-1 plasmid or protein scaffolds (solid markers and lines) have healed to a greater extent than the control or sham groups (open markers and dotted lines). Notably, 1 of 3 SDF-1 plasmid treated wounds and 2 of 5 SDF-1 protein treated wounds are 100% healed at 9 days; whereas, no control or sham wound are greater than 20% healed at 9 days.

We investigated the impact of SDF-1 on fibroblast infiltration, new blood vessel formation, and smooth muscle using immunohistochemical staining for vimentin, CD31, and smooth muscle actin, respectively. There are no substantial differences in amount of any of the stains between groups. H & E analysis showed a slight decrease in fibrosis in the SDF-1 protein and plasmid treated wounds compared to control or sham, with all other parameters being similar. The results are shown below in the following tables.

The results are shown the table below.

Wound Healing H/E Data

Day 9

| | # wounds with fibrosis | | | | | |
|---|---|---|---|---|---|---|
| Sham (no patch) | 2 | 1 | 1 | 0 | 2 (of 2) | 50% |
| Control (saline patch) | 2 | 1 | 0 | 1 | 2 (of 2) | 50% |
| SDF1 Protein Patch | 5 | 4 | 1 | 0 | 5 (of 5) | 80% |
| SDF1 Plasmid Patch | 3 | 3 | 0 | 0 | 3 (of 3) | 100% |

| | # wounds with granulomatous inflammation | | | | | |
|---|---|---|---|---|---|---|
| Sham (no patch) | 2 | 0 | 0 | | 0 (of 2) | 50% |
| Control (saline patch) | 2 | 0 | 1 | | 1 (of 2) | 50% |
| SDF1 Protein Patch | 5 | 1 | 0 | | 1 (of 5) | 80% |
| SDF1 Plasmid Patch | 3 | 0 | 0 | | 0 (of 3) | 100% |

Wound Healing H/E Data
Day 9

|  | | | | # of wounds with necrosis |
|---|---|---|---|---|
| Sham (no patch) | 2 | 1 | 0 | 1 (of 2) |
| Control (saline patch) | 2 | 0 | 0 | 0 (of 2) |
| SDF1 Protein Patch | 5 | 1 | 1 | 2 (of 5) |
| SDF1 Plasmid Patch | 3 | 1 | 0 | 1 (of 3) |

Wound Healing H/E Data
Day 9

|  | | | | # of wounds with sub-acute inflammation |
|---|---|---|---|---|
| Sham (no patch) | 2 | 1 | 1 | 0 | 2 (of 2) |
| Control (saline patch) | 2 | 0 | 0 | 0 | 0 (of 2) |
| SDF1 Protein Patch | 5 | 0 | 1 | 1 | 2 (of 5) |
| SDF1 Plasmid Patch | 3 | 1 | 0 | 1 | 2 (of 3) |

From the above description of the invention, those skilled in the art will perceive improvements, changes and modifications. Such improvements, changes and modifications within the skill of the art are intended to be covered by the appended claims. All patents, patent applications and publications cited herein are incorporated by reference in their entirety.

What is claimed:

1. A method for inhibiting and/or mitigating formation of scar tissue in a wound of the skin in which the edges are approximated, said method comprising administering directly to a said wound and/or an area proximate the wound a therapeutically effective amount of a DNA plasmid encoding SDF-1.

2. The method according to claim 1, wherein said wound of the skin is an acute wound selected from an incision or a laceration.

3. The method according to claim 1, wherein said DNA plasmid encoding SDF-1 is administered in a pharmaceutical composition that comprises said DNA plasmid encoding SDF-1 and a pharmaceutically acceptable carrier.

4. The method according to claim 3, wherein said pharmaceutical composition is an injectable formulation.

5. The method according to claim 1, wherein said DNA plasmid encoding SDF-1 is administered in the form of a topical formulation.

6. The method according to claim 1, wherein said DNA plasmid encoding SDF-1 is administered in or on a substrate, solid support or wound dressing.

7. The method according to claim 6, wherein said DNA plasmid encoding SDF-1 is administered in or on a substrate, and the substrate is in the form of a bioresorbable implant.

8. The method according to claim 1, wherein said DNA plasmid encoding SDF-1 is administered in or on a wound dressing.

9. The method according to claim 1, wherein said DNA plasmid encoding SDF-1 is administered to an external surface of the wound.

10. The method according to claim 1, wherein said DNA plasmid encoding SDF-1 is administered as part of a surgical procedure.

11. The method according to claim 1, wherein said DNA plasmid encoding SDF-1 is administered within 24 hours of the wound occurring.

12. The method according to claim 1, wherein said DNA plasmid encoding SDF-1 is administered more than 24 hours after the wound occurred.

* * * * *

```
SEQUENCE LISTING

<160> NUMBER OF SEQ ID NOS: 5

<210> SEQ ID NO 1
<211> LENGTH: 68
<212> TYPE: PRT
<213> ORGANISM: Homo sapiens

<400> SEQUENCE: 1

Lys Pro Val Ser Leu Leu Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 89
<212> TYPE: PRT
<213> ORGANISM: Homo sapiens

<400> SEQUENCE: 2

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 3
<211> LENGTH: 89
<212> TYPE: PRT
```

<213> ORGANISM: Rattus norvegicus

<400> SEQUENCE: 3

```
Met Asp Ala Lys Val Ala Val Leu Ala Leu Val Leu Ala Ala Leu
1               5                   10                  15

Cys Ile Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Ser Asn Asn Arg Gln Val Cys Ile Asp Pro Lys Leu Lys Trp Ile Gln
65                  70                  75                  80

Glu Tyr Leu Asp Lys Ala Leu Asn Lys
                85
```

<210> SEQ ID NO 4
<211> LENGTH: 1940
<212> TYPE: DNA
<213> ORGANISM: Homo sapiens

<400> SEQUENCE: 4

| | | | | | |
|---|---|---|---|---|---|
| gccgcacttt | cactctccgt | cagccgcatt | gcccgctcgg | cgtccggccc | ccgacccgcg | 60 |
| ctcgtccgcc | cgcccgcccg | cccgcccgcg | ccatgaacgc | caaggtcgtg | gtcgtgctgg | 120 |
| tcctcgtgct | gaccgcgctc | tgcctcagcg | acgggaagcc | cgtcagcctg | agctacagat | 180 |
| gcccatgccg | attcttcgaa | agccatgttg | ccagagccaa | cgtcaagcat | ctcaaaattc | 240 |
| tcaacactcc | aaactgtgcc | cttcagattg | tagcccggct | gaagaacaac | aacagacaag | 300 |
| tgtgcattga | cccgaagcta | aagtggattc | aggagtaccc | ggagaaagct | ttaaacaagt | 360 |
| aagcacaaca | gccaaaaagg | actttccgct | gacccactc | gaggaaaact | aaaaccttgt | 420 |
| gagagatgaa | agggcaaaga | cgtgggggag | ggggccttaa | ccatgaggac | caggtgtgtg | 480 |
| tgtggggtgg | gcacattgat | ctgggatcgg | gcctgaggtt | tgccagcatt | tagaccctgc | 540 |
| atttatagca | tacggtatga | tattgcagct | tatattcatc | catgccctgt | acctgtgcac | 600 |
| gttggaactt | ttattactgg | ggttttcta | agaaagaaat | tgtattatca | acagcatttt | 660 |
| caagcagtta | gttccttcat | gatcatcaca | atcatcatca | ttctcattct | cattttttaa | 720 |
| atcaacgagt | acttcaagat | ctgaatttgg | cttgtttgga | gcatctcctc | tgctcccctg | 780 |
| gggagtctgg | gcacagtcag | gtggtggctt | aacagggagc | tggaaaaagt | gtcctttctt | 840 |
| cagacactga | ggctcccgca | gcagcgcccc | tcccaagagg | aaggcctctg | tggcactcag | 900 |
| ataccgactg | gggctgggcg | ccgccactgc | cttcacctcc | tctttcaacc | tcagtgattg | 960 |
| gctctgtggg | ctccatgtag | aagccactat | tactgggact | gtgctcagag | acccctctcc | 1020 |
| cagctattcc | tactctctcc | ccgactccga | gagcatgctt | aatcttgctt | ctgcttctca | 1080 |
| tttctgtagc | ctgatcagcg | ccgcaccagc | cgggaagagg | gtgattgctg | ggctcgtgc | 1140 |
| cctgcatccc | tctcctccca | gggcctgccc | cacagctcgg | gccctctgtg | agatccgtct | 1200 |
| ttggcctcct | ccagaatgga | gctggccctc | tcctggggat | gtgtaatggt | cccctgcttt | 1260 |
| acccgcaaaa | gacaagtctt | tacagaatca | aatgcaattt | taaatctgag | agctcgcttt | 1320 |
| gagtgactgg | gttttgtgat | tgcctctgaa | gcctatgtat | gccatggagg | cactaacaaa | 1380 |
| ctctgaggtt | tccgaaatca | gaagcgaaaa | aatcagtgaa | taaccatca | tcttgccact | 1440 |
| accccctcct | gaagccacag | cagggtttca | ggttccaatc | agaactgttg | gcaaggtgac | 1500 |

-continued

```
atttccatgc ataaatgcga tccacagaag gtcctggtgg tatttgtaac tttttgcaag    1560
gcattttttt atatatattt ttgtgcacat tttttttttac gtttctttag aaaacaaatg    1620
tatttcaaaa tatatttata gtcgaacaat tcatatattt gaagtggagc catatgaatg    1680
tcagtagttt atacttctct attatctcaa actactggca atttgtaaag aaatatatat    1740
gatatataaa tgtgattgca gcttttcaat gttagccaca gtgtattttt tcacttgtac    1800
taaaattgta tcaaatgtga cattatatgc actagcaata aaatgctaat tgtttcatgg    1860
tataaacgtc ctactgtatg tgggaattta tttacctgaa ataaaattca ttagttgtta    1920
gtgatggagc ttaaaaaaaa                                                1940

<210> SEQ ID NO 5
<211> LENGTH: 293
<212> TYPE: DNA
<213> ORGANISM: Rattus norvegicus

<400> SEQUENCE: 5
ccatggacgc caaggtcgtc gctgtgctgg ccctggtgct ggccgcgctc tgcatcagtg      60
acggtaagcc agtcagcctg agctacagat gcccctgccg attctttgag agccatgtcg     120
ccagagccaa cgtcaaacat ctgaaaatcc tcaacactcc aaactgtgcc cttcagattg     180
ttgcaaggct gaaaagcaac aacagacaag tgtgcattga cccgaaatta aagtggatcc     240
aagagtacct ggacaaagcc ttaaacaagt aagcacaaca gcccaaagga ctt           293
```